United States Patent
Yuan

(10) Patent No.: US 10,588,568 B2
(45) Date of Patent: Mar. 17, 2020

(54) RUNNING GUIDING METHOD AND DEVICE

(71) Applicant: BOE TECHNOLOGY GROUP CO., LTD., Beijing (CN)

(72) Inventor: Zuo Yuan, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 185 days.

(21) Appl. No.: 15/124,514

(22) PCT Filed: Sep. 25, 2015

(86) PCT No.: PCT/CN2015/090743
§ 371 (c)(1),
(2) Date: Sep. 8, 2016

(87) PCT Pub. No.: WO2016/188001
PCT Pub. Date: Dec. 1, 2016

(65) Prior Publication Data
US 2017/0135627 A1    May 18, 2017

(51) Int. Cl.
*A61B 5/00* (2006.01)
*A61B 5/0205* (2006.01)
(Continued)

(52) U.S. Cl.
CPC ............ *A61B 5/486* (2013.01); *A61B 5/0205* (2013.01); *A61B 5/02125* (2013.01); *A61B 5/02416* (2013.01); *A61B 5/02438* (2013.01); *A61B 5/0402* (2013.01); *A61B 5/0404* (2013.01); *A61B 5/0408* (2013.01);
(Continued)

(58) Field of Classification Search
CPC .............................. A61B 5/0816; A61B 5/681
See application file for complete search history.

(56) References Cited

U.S. PATENT DOCUMENTS

| 7,001,337 B2 * | 2/2006 | Dekker ............... A61B 5/0205 600/483 |
| 8,439,844 B2 | 5/2013 | O'Rourke |

(Continued)

FOREIGN PATENT DOCUMENTS

| CN | 1242693 A | 1/2000 |
| CN | 101520815 A | 9/2009 |

(Continued)

OTHER PUBLICATIONS

Chinese Office Action dated Nov. 17, 2017.
(Continued)

*Primary Examiner* — Michael W Kahelin
(74) *Attorney, Agent, or Firm* — Dilworth & Barrese, LLP.; Michael J. Musella, Esq.

(57) ABSTRACT

A running guiding method and a running guiding device are provided, which combine a step frequency and a respiratory rate of a runner to determine whether the step frequency matches the respiratory rate of the runner. When the step frequency does not match the respiratory rate, they provide a prompt of step frequency adjustment based on the step frequency and the respiratory rate of the runner. Thus, an effective running guidance can be provided to the runner and the runner may make an adjustment based on the guidance to improve his/her running efficiency.

17 Claims, 4 Drawing Sheets

(51) Int. Cl.
  *A61B 5/11*    (2006.01)
  *A61B 5/024*   (2006.01)
  *A61B 5/021*   (2006.01)
  *A61B 5/0402*  (2006.01)
  *A61B 5/0404*  (2006.01)
  *A61B 5/0408*  (2006.01)
  *A61B 5/08*    (2006.01)

(52) U.S. Cl.
  CPC ............. *A61B 5/0816* (2013.01); *A61B 5/11* (2013.01); *A61B 5/1123* (2013.01); *A61B 5/681* (2013.01); *A61B 5/6824* (2013.01); *A61B 5/7282* (2013.01); *A61B 5/742* (2013.01); *A61B 5/02108* (2013.01); *A61B 5/02405* (2013.01); *A61B 5/112* (2013.01); *A61B 2503/10* (2013.01); *A61B 2505/09* (2013.01); *A61B 2562/0219* (2013.01)

(56) References Cited

U.S. PATENT DOCUMENTS

| | | | |
|---|---|---|---|
| 8,449,435 B2 | 5/2013 | Jang et al. | |
| 8,712,723 B1* | 4/2014 | Kahn | G01C 22/006 377/24.2 |
| 2011/0066007 A1* | 3/2011 | Banet | A61B 5/0402 600/301 |
| 2012/0235821 A1 | 9/2012 | Dibenedetto | |
| 2013/0171599 A1 | 7/2013 | Bleich et al. | |
| 2014/0357960 A1* | 12/2014 | Phillips | A61B 5/486 600/301 |
| 2015/0119725 A1 | 4/2015 | Martin et al. | |

FOREIGN PATENT DOCUMENTS

| | | |
|---|---|---|
| CN | 102138789 A | 8/2011 |
| CN | 202497679 U | 10/2012 |
| CN | 102989159 A | 3/2013 |
| CN | 103188375 A | 7/2013 |
| CN | 103892815 A | 7/2014 |
| CN | 104146446 A | 11/2014 |
| CN | 104814728 A | 8/2015 |

OTHER PUBLICATIONS

Second Chinese Office Action dated May 16, 2017.
Search Report and Written Opinion dated Feb. 25, 2016 from State Intellectual Property Office of the P.R. China.
Chinese Office Action dated Dec. 5, 2016.
Family Medical Guide—chiefly edited by the editorial committee of Shanghai Medical College of Fudan University, published on Sep. 2012, discloses (pp. 160-161).
Principle and Design of Modern Medical Electronic Instruments>, published by South China University Press of Technology on Sep. 2007 and edited by YU, Xuefei (183-187).
European Search Report dated Oct. 15, 2018.

* cited by examiner

RUNNING GUIDING METHOD AND DEVICE

TECHNICAL FIELD

Embodiments of the present disclosure relate to a running guiding method and a running guiding device.

BACKGROUND

Running is one of the exercise approaches favored by most people due to its convenience and simplicity. There are many well-known factors having influence on the running efficiency and safety of the runner, such as environment, a running field, a health status of the runner, running equipments and the like. However, many people do not know that a proper running method is also very important. When an improper running method is used, problems such as respiratory disorder, improper pace and the like may occur while running, which may lead to a lower running efficiency and may even cause damage to the body.

SUMMARY

Embodiments of the present disclosure provide a running guiding method and a running guiding device, which can provide an effective running guidance to a runner.

The running guiding method provided in embodiments of the disclosure includes: detecting acceleration speed data and a pulse wave signal associated with a runner; obtaining a step frequency of the runner based on the acceleration speed data, and obtaining a respiratory rate of the runner based on the pulse wave signal; determining whether the step frequency matches the respiratory rate of the runner; and if the step frequency does not match the respiratory rate of the runner, providing a prompt of step frequency adjustment based on the step frequency and the respiratory rate of the runner.

For example, in the above method provided by embodiments of the disclosure, determining whether the step frequency matches the respiratory rate of the runner comprises: comparing the respiratory rate of the runner with a pre-established correspondence of respiratory rates and ranges of step frequency values to determine a range of step frequency values that corresponds to the respiratory rate, and based on the determined range of step frequency values, determining whether the step frequency is in the range of step frequency values; and if the step frequency is not in the range of step frequency values, determining that the step frequency of the runner does not match the respiratory rate.

For example, the above method provided by embodiments of the disclosure further includes: detecting an electrocardiogram (ECG) signal of the runner and obtaining a heart rate of the runner based on the ECG signal; determining whether the heart rate of the runner is normal; and if the heart rate of the runner is not normal, providing a prompt of heart rate warning.

For example, the above method provided by embodiments of the disclosure further includes: calculating a blood pressure value of the runner based on the ECG signal and the pulse wave signal; determining whether the blood pressure value of the runner is normal; and if the blood pressure value of the runner is not normal, providing a prompt of blood pressure warning.

For example, in the above method provided by embodiments of the disclosure, calculating the blood pressure value of the runner based on the ECG signal and the pulse wave signal includes: determining a pulse transmission time based on the ECG signal and the pulse wave signal; and calculating the blood pressure value based on the pulse transmission time and a prestored equation of blood pressure and the pulse transmission time.

Embodiments of the disclosure also provide a running guiding device, which includes: an acceleration detecting module, a pulse-wave-signal capture module, a central processing module and a prompting module. The acceleration detecting module is configured to detect acceleration speed data of the runner and send the acceleration speed data to the central processing module; the pulse-wave-signal capture module is configured to detect a pulse wave signal of the runner and send the pulse wave signal to the central processing module; the central processing module is configured to receive the acceleration speed data and the pulse wave signal, obtain a step frequency of the runner based on the acceleration speed data, obtain a respiratory rate of the runner based on the pulse wave signal, and determine whether the step frequency of the runner matches the respiratory rate, and if the step frequency of the runner does not match the respiratory rate, provide a prompt instruction to the prompting module based on the step frequency and the respiratory rate of the runner; and the prompting module is configured to receive the prompt instruction and provide a prompt of step frequency adjustment based on the prompt instruction.

For example, in the running guiding device provided in embodiments of the disclosure, the central processing module is further configured to store a pre-established table of correspondence between respiratory rates and ranges of step frequency values; the central processing module determines whether the step frequency of the runner matches the respiratory rate by: comparing the respiratory rate of the runner with the table of correspondence to determine a range of step frequency values corresponding to the respiratory rate, and determining whether the step frequency is in the range of step frequency values based on the determined range of step frequency values, and if the step frequency is not in the range of step frequency values, determining that the step frequency of the runner does not match the respiratory rate.

For example, the running guiding device provided in embodiments of the disclosure further includes: an electrocardiogram (ECG) signal capture module. The electrocardiogram signal capture module is configured to detect an ECG signal of the runner and send the ECG signal to the central processing module; the central processing module is further configured to receive the ECG signal, obtain a heart rate of the runner based on the ECG signal, and determine whether the heart rate of the runner is normal, and if the heart rate of the runner is not normal, provide an instruction of heart rate warning to the prompting module; and the prompting module is further configured to receive the instruction of heart rate warning, and provide a prompt of heart rate warning based on the instruction of heart rate warning.

For example, in the running guiding device provided in embodiments of the disclosure, the central processing module is further configured to calculate a blood pressure value of the runner based on the ECG signal and the pulse wave signal, and determine whether the blood pressure value of the runner is normal, and if the blood pressure value of the runner is not normal, provide an instruction of blood pressure warning to the prompting module; and the prompting module is further configured to receive the instruction of blood pressure warning, and provide a prompt of blood pressure warning based on the instruction of blood pressure warning.

For example, in the running guiding device provided in embodiments of the disclosure, the central processing module calculates the blood pressure value of the runner based on the ECG signal and the pulse wave signal at least by: determining a pulse transmission time based on the ECG signal and the pulse wave signal; and calculating the blood pressure value based on the pulse transmission time and a prestored equation of blood pressure and the pulse transmission time.

For example, in the running guiding device provided in embodiments of the disclosure, the acceleration detecting module includes a tri-axial accelerometer; and/or the pulse-wave-signal capture module includes a photoelectric transducer.

For example, in the running guiding device provided in embodiments of the disclosure, the electrocardiogram signal capture module comprises an ECG electrode and an ECG sensor that are electrically connected with each other, the ECG electrode is configured to contact with the runner to capture a signal, and the ECG sensor is configured to convert the signal captured by the ECG electrode into an ECG signal and send the ECG signal to the central processing module.

For example, the running guiding device provided in embodiments of the disclosure further includes: a display. The central processing module is further configured to send body sign parameters to the display in real time, wherein the body sign parameters comprise the step frequency, the respiratory rate, the heart rate and the pressure value; and the display is configured to show the body sign parameters of the runner in real time.

For example, the running guiding device provided in embodiments of the disclosure further includes: a data transmitting module. The central processing module is further configured to store the body sign parameters of the runner; the data transmitting module is configured to send the body sign parameters stored by the central processing module to a smart terminal.

For example, in the running guiding device provided in embodiments of the disclosure, the running guiding device is a watch, a bracelet or an armlet.

The running guiding method and running guiding device provided in embodiments of the disclosure combine a step frequency and a respiratory rate of a runner to determine whether the step frequency matches the respiratory rate of the runner. When the step frequency does not match the respiratory rate, they provide a prompt of step frequency adjustment based on the step frequency and the respiratory rate of the runner. Thus, an effective running guidance can be provided to the runner and the runner may make an adjustment based on the guidance to improve his/her running efficiency.

BRIEF DESCRIPTION OF THE DRAWINGS

In order to illustrate the technical solutions in the embodiments of the present disclosure or the existing arts more clearly, the drawings need to be used in the description of the embodiments or the existing arts will be briefly described in the following; it is obvious that the drawings described below are only related to some embodiments of the present disclosure, for one ordinary skilled person in the art, other drawings can be obtained according to these drawings without making other inventive work.

DETAILED DESCRIPTION

Hereafter, the technical solutions of the embodiments of the present disclosure will be described in a clearly and fully understandable way in connection with the drawings related to the embodiments of the disclosure. It is obvious that the described embodiments are just a part but not all of the embodiments of the present disclosure. Based on embodiments of the present disclosure, all other embodiments obtained by those skilled in the art without making other inventive work should be within the scope of the present disclosure.

Presently, intelligent devices applied in running can merely achieve a simple step-counting or heart rate detecting function, but cannot monitor more body sign parameters. Therefore, they cannot provide effective running guidance and thus brings less help to the runners.

A detailed description will be made to the specific embodiments of the running guiding method and the running guiding device provided by embodiments of the present disclosure in the following in conjunction with the drawings.

Figure 1:
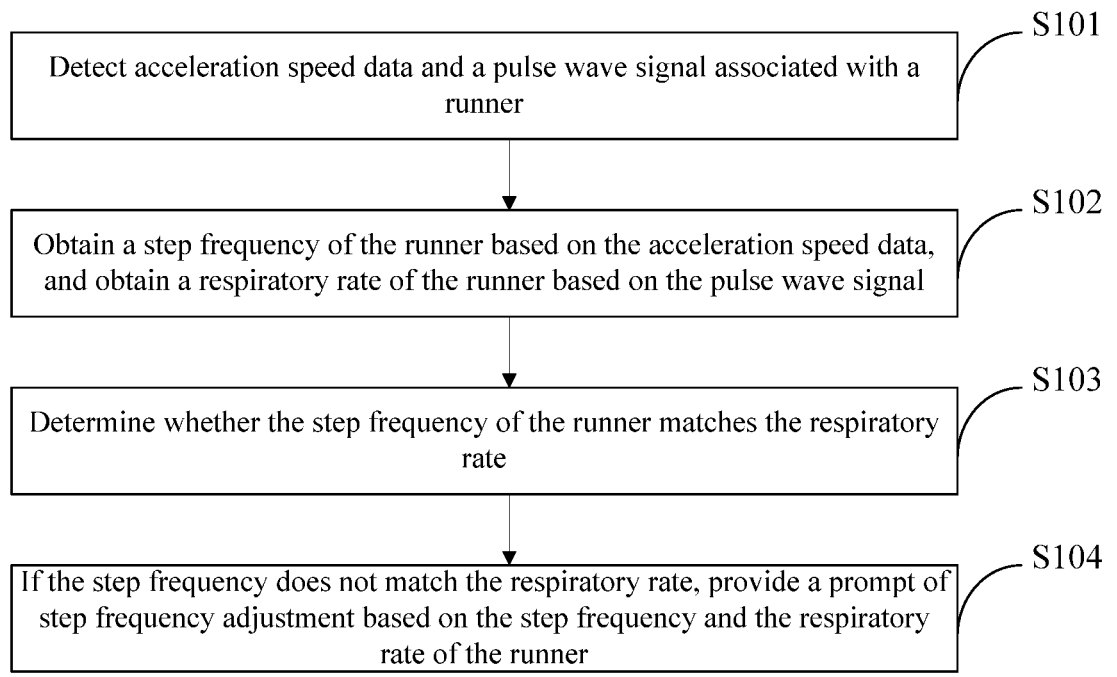
FIG. 1 is a flow chart of a running guiding method provided by an embodiment of the present disclosure.

A running guiding method provided by an embodiment of the present disclosure, as shown in FIG. 1, comprises:

S101: detecting acceleration speed data and a pulse wave signal associated with a runner;

S102: obtaining a step frequency of the runner based on the acceleration speed data, and obtaining a respiratory rate of the runner based on the pulse wave signal;

S103: determining whether the step frequency of the runner matches the respiratory rate;

S104: if the step frequency does not match the respiratory rate, providing a prompt of step frequency adjustment based on the step frequency and the respiratory rate of the runner.

The above running guiding method provided by the embodiment of the present disclosure combines the step frequency and the respiratory rate of the runner to determine whether the step frequency matches the respiratory rate of the runner. When the step frequency does not match the respiratory rate, it provides a prompt of step frequency adjustment based on the step frequency and the respiratory rate of the runner. Thus, an effective running guidance can be provided to the runner and the runner may make an adjustment based on the guidance to improve his/her running efficiency.

For example, in the above method provided by the embodiment of the present disclosure, determining whether the step frequency match the respiratory rate of the runner comprises: comparing the respiratory rate of the runner with a pre-established correspondence between respiratory rates and ranges of step frequency values to determine a range of step frequency values that corresponds to the current respiratory rate; based on the determined range of step frequency values, determining whether the step frequency of the runner is in the range of step frequency values; and if not, determining that the step frequency of the runner doesn't match the respiratory rate.

The embodiment of the present disclosure makes it possible to determine the range of step frequency values corresponding to the current respiratory rate, based on a pre-established correspondence between respiratory rates and ranges of step frequency values that is established according to physicians' suggestion or normal human physical characteristics (or, a correspondence established in other manners, and no restriction being made in this respect). For example, when a guidance is given in a pace of making an exhalation after three steps and then making an inhalation after another three steps, the correspondence between respiratory rates and ranges of step frequency values may be established as: for a respiratory rate of 15~20 times per minute, its corresponding step frequency is 90~120 steps per minute; for a respiratory rate of 20~30 times per minute, its corresponding step frequency is 120~180 steps per minute; and for a respiratory rate of 30~35 times per minute, its corresponding step frequency is 180~210 steps per minute. The above examples are only for illustrative purposes, rather than limiting the protection scope of the present disclosure.

Furthermore, in the above method provided by the embodiment of the present disclosure, providing a prompt of step frequency adjustment based on the step frequency and the respiratory rate of the runner may comprise the following manners: when the step frequency of the runner is below the range of step frequency values, then providing a prompt of increasing the step frequency; when the step frequency is above the range of step frequency values, then providing a prompt of slowing down the step frequency.

Figure 2:
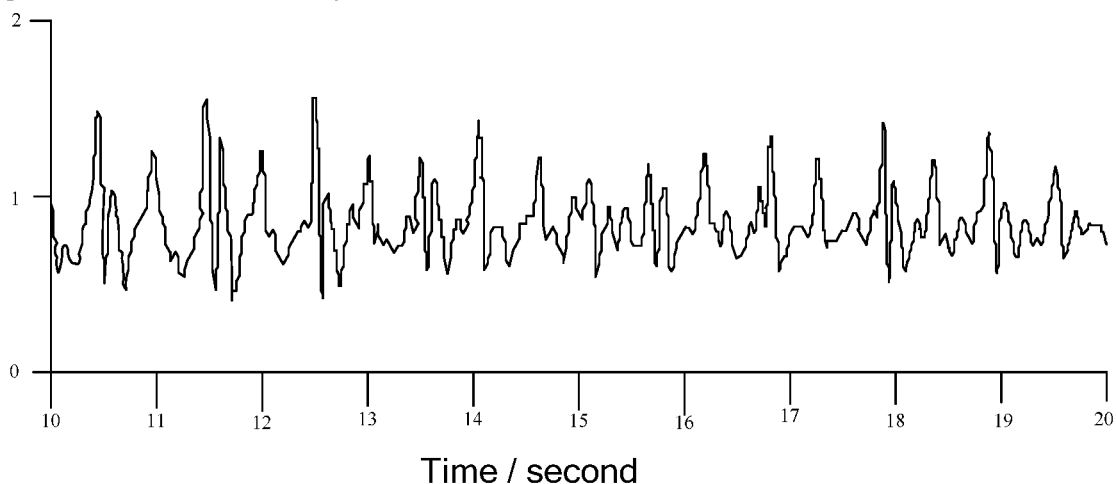
FIG. 2 is a schematic view showing fluctuation of an amplitude of an acceleration speed that varies over time during a running process provided by an embodiment of the present disclosure.

In the above method provided by the embodiment of the present disclosure, a tri-axial accelerometer may be used to capture the acceleration speed data of the runner. As shown in FIG. 2, which is a view of the amplitude of the acceleration speed of the runner varying over time during the running process. Through a method of threshold determination, it is able to recognize each step, and thus to obtain a step frequency in the process of running by calculating the number of steps per unit of time. Of course, it is also possible to obtain the acceleration speed data and the step frequency through other methods, and no restriction is made in this respect.

Figure 3:
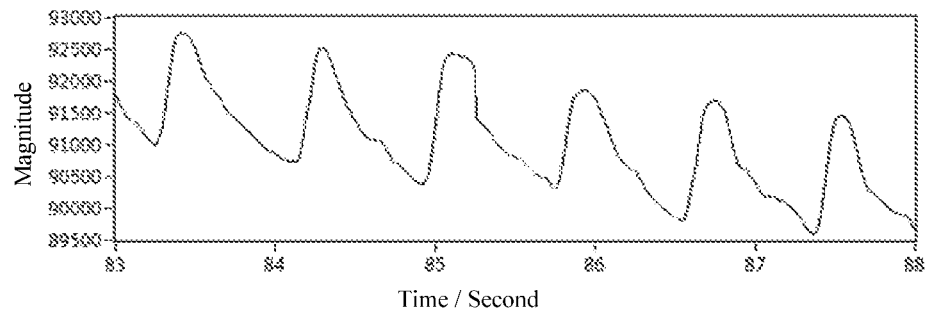
FIG. 3 is a schematic view showing a pulse wave signal provided by an embodiment of the present disclosure.
Figure 4:
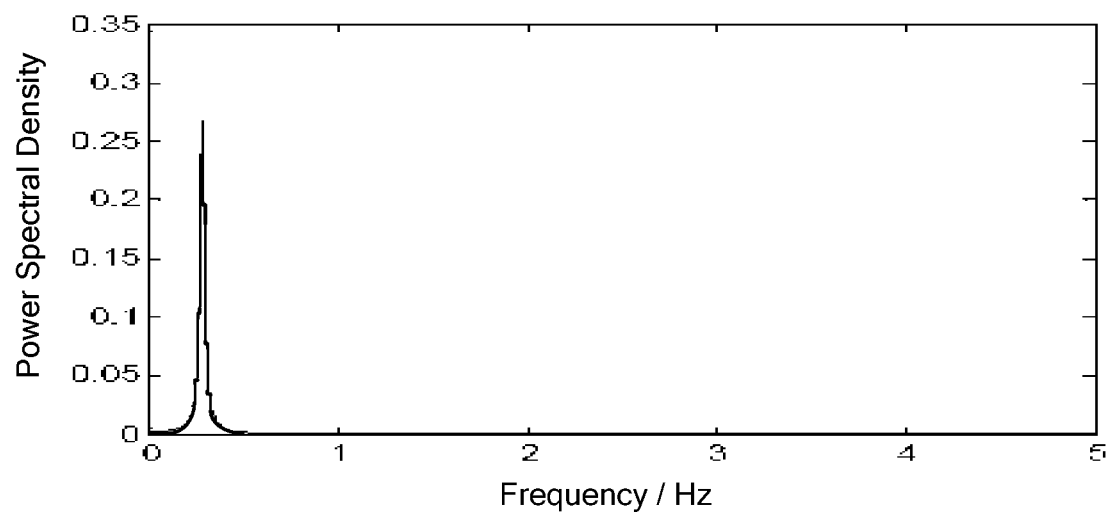
FIG. 4 is a schematic view showing a respiration spectrum obtained by performing Fourier transform on a pulse wave signal provided by an embodiment of the present disclosure.

For example, as shown in FIG. 2, a dynamic adaptive threshold may be preset, and this threshold can be updated in every 3 seconds. A value of this threshold may be an average of a maximal value and a minimal value of the acceleration speed within the last 3 seconds. Then the number of steps can be recognized based on this threshold. When the acceleration speed value passes through a line of the threshold in an upward direction (that is, the acceleration speed value at a previous moment is less than the threshold while the acceleration speed value at the current moment is greater than the threshold), it is considered that one step is detected. Then, a time difference of this step and a previous step is obtained. When the time difference is 0.2~2 seconds, it is considered that the detected step is a valid step; otherwise, the detected step is considered to be invalid and is not counted in the number of steps. In this way, one step is recognized. In the above method provided by the embodiment of the present disclosure, for example, a photoelectric transducer may be used to capture the pulse wave signal, as shown in FIG. 3. By performing Fourier transform on the captured pulse wave signal, a respiration spectrum can be obtained. As shown in FIG. 4, a peak in the spectrum within 1 Hz corresponds to a frequency which is the respiratory rate (about 0.35 Hz in the figure; that is, 0.35 times per second), and therefore, the number of breaths per minute is 0.35*60, i.e., 21 times. Of course, other methods are also possible for obtaining the pulse wave signal and the respiratory rate, and no restriction is made in this respect.

Furthermore, for example, the above method provided by the embodiment of the present disclosure may further comprise: detecting an electrocardiogram (ECG) signal of the runner and obtaining a heart rate of the runner based on the ECG signal; determining whether the heart rate of the runner is normal; if not, providing a heart rate warning.

It is noted that determining whether the heart rate of the runner is normal may include: determining whether the heart rate of the runner is in a safe range and whether a sudden change occurs to the heart rate. No restriction is made in this respect.

Furthermore, for example, the above method provided by the embodiment of the present disclosure may further comprise: calculating a blood pressure value of the runner based on the ECG signal and the pulse wave signal; determining whether the blood pressure value of the runner is normal; if not, providing a warning of blood pressure. Therefore, the runner could slow down or stop exercise based on the warning.

It is noted that determining whether the blood pressure value of the runner is normal may include determining whether the blood pressure value of the runner is in a safe range and whether a sudden change occurs to the blood pressure value. No restriction is made in this respect.

For example, in the above method provided by the embodiment of the present disclosure, calculating the blood pressure value of the runner based on the ECG signal and the pulse wave signal may comprise: determining a pulse transmission time based on the ECG signal and the pulse wave signal; calculating the blood pressure value based on the pulse wave transmission time and a prestored equation of the blood pressure and the pulse transmission time.

It is noted that the equation of the blood pressure and pulse transmission time is identical to existing equations of the blood pressure and the pulse transmission time, which is not repeated here.

Figure 5:
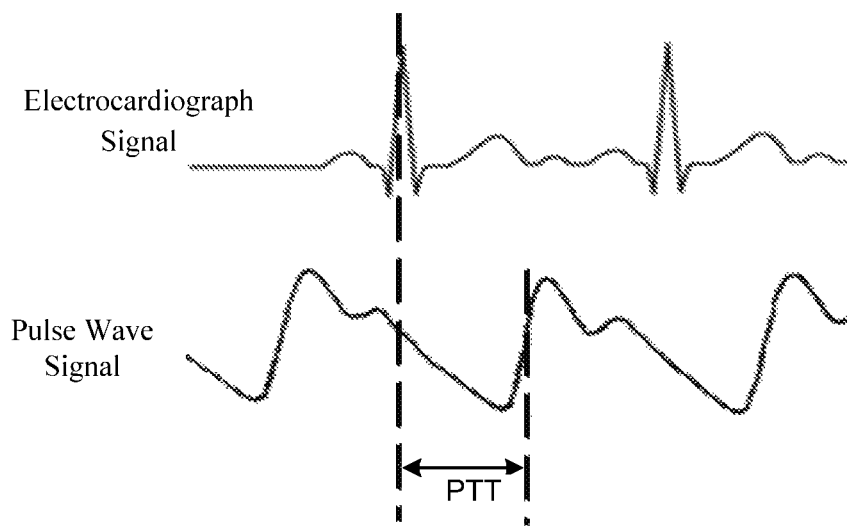
FIG. 5 is a schematic view showing relationship between a pulse transmission time and an electrocardiograph (ECG) signal of a pulse wave signal provided by an embodiment of the present disclosure.

For example, in the above method provided by the embodiment of the present disclosure, determining the pulse transmission time based on the ECG signal and the pulse wave signal may include: as shown in FIG. 5, taking a time difference from a wave peak of the ECG signal to a point of a rising branch of the pulse wave signal that has a maximal slope value as the pulse transmission time (PTT).

Figure 6:
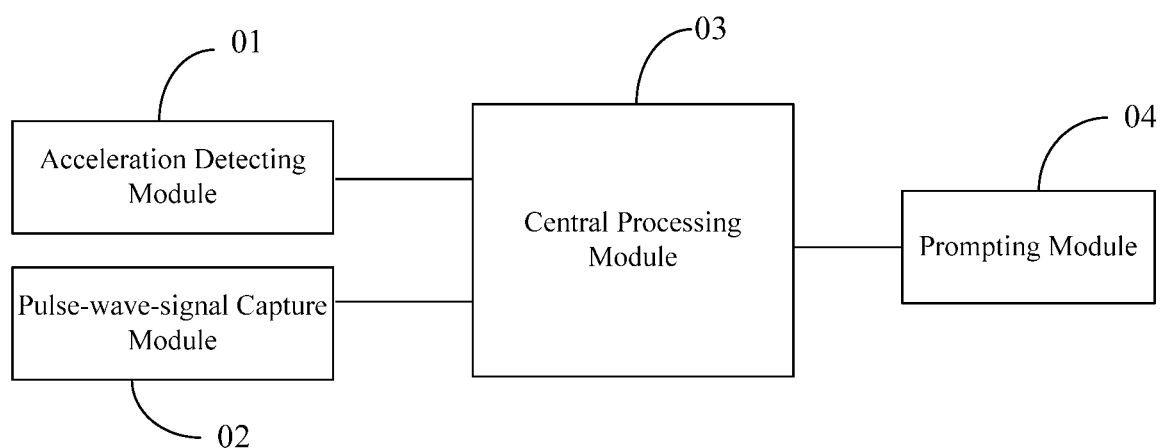
FIG. 6 is a first structural schematic view of a running guiding device provided by an embodiment of the present disclosure.

Embodiments of the present disclosure also provide a running guiding device which, as shown in FIG. 6, comprises: an acceleration detecting module 01, a pulse-wave-signal capture module 02, a central processing module 03 and a prompting module 04.

The acceleration detecting module 01 is used to detect acceleration speed data of the runner, and to send acceleration speed data to the central processing module 03; the pulse-wave-signal capture module 02 is used to detect the pulse wave signal of the runner and send the pulse wave signal to the central processing module 03; the central processing module 03 is used to receive the acceleration speed data and the pulse wave signal, obtain a step frequency of the runner based on the acceleration speed data, obtain a respiratory rate of the runner based on the pulse wave signal, and determine whether the step frequency matches the respiratory rate of the runner. If the step frequency does not match the respiratory rate of the runner, the central processing module 03 provides a prompt instruction to the prompting module 04 based on the step frequency and the respiratory rate of the runner. The prompting module 04 is used to receive the prompt instruction, and provide a prompt of step frequency adjustment based on the prompt instruction.

For example, the above running guiding device provided by the embodiment of the present disclosure comprises: an acceleration detecting module, a pulse-wave-signal capture module, a central processing module and a prompting module. The acceleration detecting module is used to detect acceleration speed data of the runner and send the acceleration speed data to the central processing module; the pulse-wave-signal capture module is used to detect the pulse wave signal of the runner and send the pulse wave signal to the central processing module; the central processing module is used to receive the acceleration speed data and the pulse wave signal, obtain the step frequency of the runner based on the acceleration speed data, obtain the respiratory rate of the runner based on the pulse wave signal, and determine whether the step frequency of the runner matches the respiratory rate. If the step frequency does not match the respiratory rate of the runner, the central processing module provides a prompt instruction to the prompting module based on the step frequency and the respiratory rate of the runner. The prompting module is used to receive the prompt instruction, and provide a prompt of step frequency adjustment based on the prompt instruction. Therefore, an effective running guidance for the runner is provided, and thus, the runner could make an adjustment based on the guidance and thereby improve her/his running efficiency.

For example, in the above running guiding device provided by the embodiment of the present disclosure, the central processing module is further used to store a pre-established table of correspondence between the respiratory rates and the ranges of the step frequency values (for example, the central processing module comprises a memory for storing the pre-established table of correspondence between the respiratory rates and the ranges of the step frequency values).

The central processing module determines whether the step frequency and the respiratory rate of the runner match with each other; for example, its operation comprises: comparing the respiratory rate of the runner with the table of correspondence to determine a range of step frequency values corresponding to the respiratory rate, and based on the determined range of step frequency values, determining whether the step frequency is in the range of step frequency values. If not, it is determined that the step frequency and the respiratory rate of the runner do not match.

Furthermore, for example, in the above running guiding device provided by the embodiment of the present disclosure, when the step frequency and the respiratory rate of the runner do not match, the central processing module is used to provide a first prompt instruction to the prompting module when the step frequency is below the range of step frequency values, or provide a second prompt instruction to the prompting module when the step frequency is above the range of step frequency values; the prompting module is used to provide a prompt of speeding up the step frequency when receiving the first prompt instruction, or provide a prompt of slowing down the step frequency when receiving the second prompt instruction.

Figure 7:
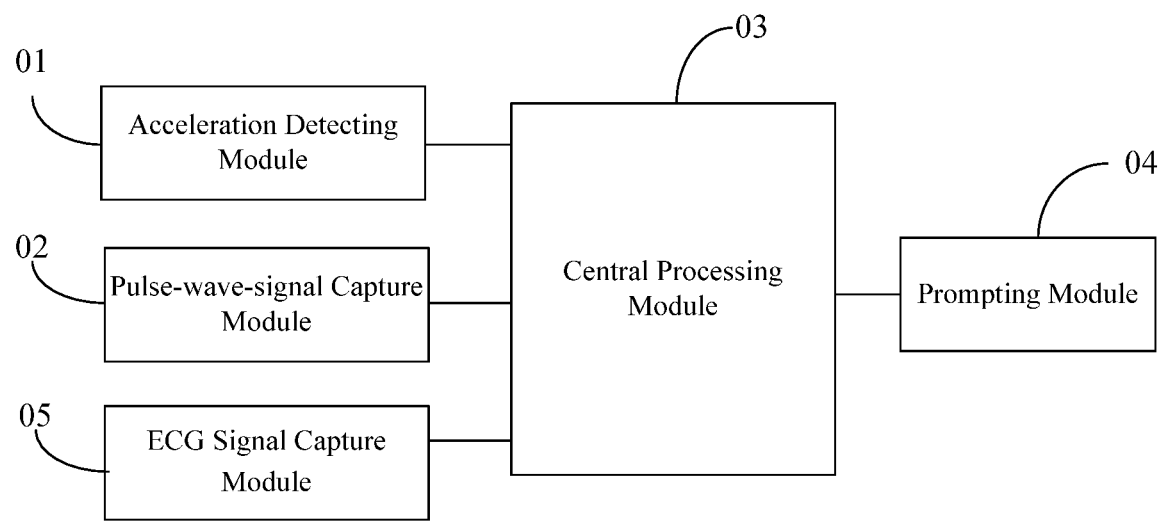
FIG. 7 is a second structural schematic view of a running guiding device provided by an embodiment of the present disclosure.

As shown in FIG. 7, the above running guiding device provided by the embodiment of the present disclosure may further comprise an electrocardiogram (ECG) signal capture module 05. The ECG signal capture module 05 is used to detect the ECG signal of the runner, and send the ECG signal to the central processing module 03; the central processing module 03 is used to receive the ECG signal, and obtain a heart rate of the runner based on the ECG signal, and then determine whether the heart rate of the runner is normal. If the heart rate of the runner is abnormal, the central processing module 03 provides an instruction of a heart rate warning to the prompting module 04; the prompting module 04 is further used to receive the instruction of heart rate warning, and provide a prompt of heart rate warning based on the instruction of heart rate warning.

In the above running guiding device provided by the embodiment of the present disclosure, the central processing module may also be used to calculate a blood pressure value of the runner based on the ECG signal and the pulse wave signal, and determine whether the blood pressure value of the runner is normal; if the blood pressure value of the runner is abnormal, the central processing module provides an instruction of blood pressure warning to the prompting module; the prompting module is further used to receive the instruction of blood pressure warning, and provide a prompt of blood pressure warning based on the instruction of blood pressure warning.

For example, in the above running guiding device provided by the embodiment of the present disclosure, the central processing module calculates the blood pressure value of the runner based on the ECG signal and the pulse wave signal, which may comprise: determining the pulse transmission time based on the ECG signal and the pulse wave signal; and calculating the blood pressure value based on the pulse wave transmission time and a prestored equation of the blood pressure and the pulse transmission time.

It is noted that the equation of the blood pressure and pulse transmission time is identical to existing equations of the blood pressure and the pulse transmission time, and its description is not repeated here.

Furthermore, in the above running guiding device provided by the embodiment of the present disclosure, the determination of the pulse transmission time based on the ECG signal and the pulse wave signal may be as shown in FIG. 5, in which a time difference from a wave peak of the ECG signal to a point of the rising waveform of the pulse wave signal with a maximal slope value is taken as the pulse transmission time (PTT).

In the above running guiding device provided by the embodiment of the present disclosure, a tri-axial accelerometer may be used for the acceleration detecting module. Due to the fact that the tri-axial accelerometer is relatively small, it is possible to reduce an overall dimension of the running guiding device. Of course, the acceleration detecting module of the present disclosure may also be implemented by other devices capable of achieving the acceleration detection, and no restriction is made in this respect.

In the above running guiding device provided by the embodiment of the present disclosure, the pulse-wave-signal capture module may be a photoelectric transducer, which may be a reflective photoelectric transducer or a transmissive photoelectric transducer, and no restriction is made in this respect. Since the photoelectric transducer is relatively small, it is possible to reduce the overall dimension of the running guiding device. Of course, the pulse-wave-signal capture module of the present disclosure may also be implemented by other devices capable of achieving the capture of the pulse wave signal, and no restriction is made in this respect.

In the above running guiding device provided by the embodiment of the present disclosure, the ECG signal capture module comprises an ECG electrode and an ECG sensor that are electrically connected with each other, where the ECG electrode is used to contact with the runner to capture a signal, and the ECG sensor is used to convert the signal captured by the ECG electrode into an ECG signal and send the ECG signal to the central processing module. Of course, the ECG signal capture module of the present disclosure may also be implemented by other devices capable of achieving the capture of the ECG signal, and no restriction is made in this respect.

For example, the above running guiding device provided by the embodiment of the present disclosure may further comprise a display; the central processing module is further used to send body sign parameters of the runner to the display in real time or in near real time, where the body sign parameters comprise the step frequency, the respiratory rate, the heart rate and the blood pressure value, etc.; the display is used to show the body sign parameters of the runner in real time or in near real time, thereby facilitating the review of the runner.

For example, the above running guiding device provided by the embodiment of the present disclosure may further comprise a data transmitting module; the central processing module is further used to store the body sign parameters of the runner; the data transmitting module is used to send the body sign parameters stored by the central processing module to a smart terminal (for example, a smart cellphone).

For example, the data transmitting module may send the body sign parameters stored by the central processing module to the smart terminal in an infrared, blue-tooth, or WI-FI manner and the like.

Furthermore, for example, the above running guiding device provided by the embodiment of the present disclosure may further comprise: a power supply module for providing power to the above various modules. For example, the power supply module may be implemented as a rechargeable lithium battery.

Furthermore, for example, in the above running guiding device provided by the embodiment of the present disclosure, the prompting module may perform prompting and warning in a voice manner.

Furthermore, the above running guiding device provided by the embodiment of the present disclosure may enable a highly integration of the various modules, and therefore the above running guiding device may be in a product form such as a watch, a bracelet or an armlet and similar wearable devices, and thus requirements of miniaturization, portability and lower power consumption are satisfied.

The running guiding method and the running guiding device provided by the embodiments of the present disclosure combine the step frequency and the respiratory rate of the runner to determine whether the step frequency matches the respiratory rate of the runner. When the step frequency does not match the respiratory rate, a prompt of step frequency adjustment is provided based on the step frequency and the respiratory rate of the runner. Thus, an effective running guidance is provided for the runner, and the runner could make an adjustment based on the guidance, thereby improving her/his running efficiency.

The running guiding device provided by the embodiments of the present disclosure may further include one or more processors and one or more memories. The processor may process data signals and may include various computing architectures such as a complex instruction set computer (CISC) architecture, a reduced instruction set computer (RISC) architecture or an architecture for implementing a combination of multiple instruction sets. The memory may store instructions and/or data executed by the processor. The instructions and/or data may include codes which are configured to achieve some functions or all the functions of one or more devices in the embodiments of the present disclosure. For instance, the memory includes a dynamic random access memory (DRAM), a static random access memory (SRAM), a flash memory, an optical memory or other memories well known to those skilled in the art.

In some embodiments of the present disclosure, the central processing module and/or the prompting module may include codes and programs stored in the memories; and the processors may execute the codes and the programs to achieve some functions or all the functions of the central processing module and/or the prompting module.

In some embodiments of the present disclosure, the central processing module and/or the prompting module may be specialized hardware devices and configured to achieve some or all the functions of the central processing module and/or the prompting module. For instance, the central processing module and/or the prompting module may be a circuit board or a combination of a plurality of circuit boards and configured to achieve the above functions. In embodiments of the present disclosure, the circuit board or a combination of the plurality of circuit boards may include: (1) one or more processors; (2) one or more non-transitory computer-readable memories connected with the processors; and (3) processor-executable firmware stored in the memories.

It's to be noted that, in the drawings, for the clarity of the drawings the sizes of layers and areas may be exaggerated. And it can be understood, in the case that a component or a layer called "on" another element or layer, it can be directly on the top of the other elements, or can exist in the middle layer. Besides, it can be understood that, in the case that a component or a layer called "under" another element or layer, it can be directly under the other components, or there are at least two intermediate layers or elements. Besides, it can also be understood that, in the case that a layer or a component called "between" two layers or two elements, it can be the only layer of the two layers or two components, or it also exists at least two intermediate layers or elements. The similar reference marks indicate similar components in the whole text.

In the present disclosure, terms such as "first", "second" and the like used in the present disclosure do not indicate any sequence, quantity or significance but only for distinguishing different constituent parts. Also, the terms such as "a," "an," or "the" etc., are not intended to limit the amount, but indicate the existence of at lease one. The terms "comprises," "comprising," "includes," "including," etc., are intended to specify that the elements or the objects stated before these terms encompass the elements or the objects and equivalents thereof listed after these terms, but do not preclude the other elements or objects.

It is noted that, azimuth or positional relationships indicated by terms such as "up" and "down" and so on, are azimuth or positional relationships based on the drawings, which are only to facilitate description of the embodiments of the present disclosure and simplify the description, but not to indicate or imply that the devices or components must have a specific azimuth, or be constructed or operated in the specific azimuth, which thus cannot be understood as a limitation to the embodiments of the present disclosure. Unless otherwise clearly defined and limited, terms such as "installed", "coupled", "connected" should be broadly interpreted, for example, it may be fixedly connected, or may be detachably connected, or integrally connected; it may be mechanically connected, or may be electrically connected; it may be directly connected, or may be indirectly connected via an intermediate medium. Those skilled in the art can understand the specific meanings of the above-mentioned terms in the embodiments of the present disclosure according to the specific circumstances.

Obviously, those skilled in the art may modify the disclosure in various ways without breaking away from the spirits and scope of the disclosure. And so, if these changes and variations of the disclosure also fall within the scope of the claims or their equivalent technologies, the disclosure intends to include these changes and variations.

What are described above is related to the illustrative embodiments of the disclosure only and not limitative to the scope of the disclosure; any changes or replacements easily for those technical personnel who are familiar with this technology in the field to envisage in the scopes of the disclosure, should be in the scope of protection of the present disclosure. Therefore, the scopes of the disclosure are defined by the accompanying claims.

The present application claims the priority of the Chinese Patent Application No. 201510282892.3 filed on May 28, 2015, which is incorporated herein by reference in its entirety as part of the disclosure of the present application.

What is claimed is:

1. A running guiding method, comprising:
   detecting acceleration data and a pulse wave signal associated with a runner;
   obtaining a step frequency of the runner based on the acceleration data, and obtaining a respiratory rate of the runner based on the pulse wave signal;
   determining whether the step frequency matches the respiratory rate of the runner; and
   if the step frequency does not match the respiratory rate of the runner, providing a prompt of step frequency adjustment based on the step frequency and the respiratory rate of the runner;
   wherein, obtaining a step frequency of the runner based on the acceleration data comprises: presetting a dynamic adaptive threshold and a time difference range, wherein the time difference range ranges from 0.2 seconds to 2 seconds, the dynamic adaptive threshold is updated in every 3 seconds, and a value of the dynamic adaptive threshold is an average of a maximal value and a minimal value of the acceleration data within the 3 seconds; determining that the runner performs one current step when a value of the acceleration data at a previous moment is less than the dynamic adaptive threshold and a value of the acceleration data at a current moment is greater than the dynamic adaptive threshold; determining a time difference, wherein the time difference is a time interval between a previous step and the current step, and the previous step and the current step are adjacent; determining that the runner performs a valid step at the current moment when the time difference between adjacent the previous step and the current step is within the time difference range; and obtaining the step frequency of the runner by calculating a quantity of valid steps per unit of time.

2. The method according to claim 1, wherein determining whether the step frequency matches the respiratory rate of the runner comprises:
   comparing the respiratory rate of the runner with a pre-established correspondence of respiratory rates and ranges of step frequency values to determine a range of step frequency values that corresponds to the respiratory rate, and based on the determined range of step frequency values, determining whether the step frequency is in the range of step frequency values; and
   if the step frequency is not in the range of step frequency values, determining that the step frequency of the runner does not match the respiratory rate.

3. The method according to claim 1, further comprising:
   detecting an electrocardiogram (ECG) signal of the runner and obtaining a heart rate of the runner based on the ECG signal;
   determining whether the heart rate of the runner is normal; and
   if the heart rate of the runner is not normal, providing a prompt of heart rate warning.

4. The method according to claim 3, further comprising:
   calculating a blood pressure value of the runner based on the ECG signal and the pulse wave signal;
   determining whether the blood pressure value of the runner is normal; and
   if the blood pressure value of the runner is not normal, providing a prompt of blood pressure warning.

5. The method according to claim 4, wherein calculating the blood pressure value of the runner based on the ECG signal and the pulse wave signal comprises:
   determining a pulse transmission time based on the ECG signal and the pulse wave signal; and
   calculating the blood pressure value based on the pulse transmission e and a prestored equation of blood pressure and the pulse transmission time.

6. The method according to claim 2, further comprising:
   detecting an electrocardiogram (ECG) signal of the runner and obtaining a heart rate of the runner based on the ECG signal;
   determining whether the heart rate of the runner is normal; and
   if the heart rate of the runner is not normal, providing a prompt of heart rate warning.

7. A running guiding device, comprising: an acceleration detecting module, a pulse-wave-signal capture module, a central processing module and a prompting module; wherein:
   the acceleration detecting module is configured to detect acceleration data of the runner and send the acceleration data to the central processing module;
   the pulse-wave-signal capture module is configured to detect a pulse wave signal of the runner and send the pulse wave signal to the central processing module;
   the central processing module is configured to receive the acceleration data and the pulse wave signal, obtain a step frequency of the runner based on the acceleration data, obtain a respiratory rate of the runner based on the pulse wave signal, and determine whether the step frequency of the runner matches the respiratory rate, and when the step frequency of the runner does not match the respiratory rate, provide a prompt instruction to the prompting module based on the step frequency and the respiratory rate of the runner; and the prompting module is configured to receive the prompt instruction and provide a prompt of step frequency adjustment based on the prompt instruction;

wherein when performing an operation of obtaining a step frequency of the runner based on the acceleration data, the central processing module is configured to: presetting a dynamic adaptive threshold and a time difference range, wherein the time difference range ranges from 0.2 seconds to 2 seconds, the dynamic adaptive threshold is updated in every 3 seconds, and a value of the dynamic adaptive threshold is an average of a maximal value and a minimal value of the acceleration data within the 3 seconds; determining that the runner performs one current step when a value of the acceleration data at a previous moment is less than the dynamic adaptive threshold and a value of the acceleration data at a current moment is greater than the dynamic adaptive threshold; determining a time difference, wherein the time difference is a time interval between a previous step and the current step, and the previous step and the current step are adjacent; determining that the runner performs a valid step at the current moment when the time difference between adjacent the previous step and the current step is within the time difference range; and obtaining the step frequency of the runner by calculating a quantity of valid steps per unit of time.

8. The running guiding device according to claim 7, wherein the central processing module is further configured to store a pre-established table of correspondence between respiratory rates and ranges of step frequency values;

the central processing module determines whether the step frequency of the runner matches the respiratory rate by: comparing the respiratory rate of the runner with the table of correspondence to determine a range of step frequency values corresponding to the respiratory rate, and determining whether the step frequency is in the range of step frequency values based on the determined range of step frequency values, and when the step frequency is not in the range of step frequency values, determining that the step frequency of the runner does not match the respiratory rate.

9. The running guiding device according to claim 7, further comprising: an electrocardiogram (ECG) signal capture module; wherein:

the electrocardiogram signal capture module is configured to detect an ECG signal of the runner and send the ECG signal to the central processing module;

the central processing module is further configured to receive the ECG signal, obtain a heart rate of the runner based on the ECG signal, and determine whether the heart rate of the runner is normal, and if the heart rate of the runner is not normal, provide an instruction of heart rate warning to the prompting module; and the prompting module is further configured to receive the instruction of heart rate warning, and provide a prompt of heart rate warning based on the instruction of heart rate warning.

10. The running guiding device according to claim 9, wherein:

the central processing module is further configured to calculate a blood pressure value of the runner based on the ECG signal and the pulse wave signal, and determine whether the blood pressure value of the runner is normal, and when the blood pressure value of the runner is not normal, provide an instruction of blood pressure warning to the prompting module; and the prompting module is further configured to receive the instruction of blood pressure warning, and provide a prompt of blood pressure warning based on the instruction of blood pressure warning.

11. The running guiding device according to claim 10, wherein the central processing module calculates the blood pressure value of the runner based on the ECG signal and the pulse wave signal at least by:

determining a pulse transmission time based on the ECG signal and the pulse wave signal; and calculating the blood pressure value based on the pulse transmission time and a prestored equation of blood pressure and the pulse transmission time.

12. The running guiding device according to claim 7, wherein the acceleration detecting module includes a tri-axial accelerometer.

13. The running guiding device according to claim 9, wherein the electrocardiogram signal capture module comprises an ECG electrode and an ECG sensor that are electrically connected with each other, the ECG electrode is configured to contact with the runner to capture a signal, and the ECG sensor is configured to convert the signal captured by the ECG electrode into an ECG signal and send the ECG signal to the central processing module.

14. The running guiding device according to claim 10, further comprising: a display; wherein:

the central processing module is further configured to send body sign parameters to the display in real time, wherein the body sign parameters comprise the step frequency, the respiratory rate, the heart rate and the pressure value; and the display is configured to show the body sign parameters of the runner in real time.

15. The running guiding device according to claim 14, further comprising: a data transmitting module; wherein:

the central processing module is further configured to store the body sign parameters of the runner;

the data transmitting module is configured to send the body sign parameters stored by the central processing module to a smart terminal.

16. The running guiding device according to claim 7, wherein the running guiding device is a watch, a bracelet or an armlet.

17. The running guiding device according to claim 7, wherein the pulse-wave-signal capture module includes a photoelectric transducer.

* * * * *

UNITED STATES PATENT AND TRADEMARK OFFICE
CERTIFICATE OF CORRECTION

PATENT NO. : 10,588,568 B2  
APPLICATION NO. : 15/124514  
DATED : March 17, 2020  
INVENTOR(S) : Zuo Yuan Page 1 of 1

It is certified that error appears in the above-identified patent and that said Letters Patent is hereby corrected as shown below:

On the Title Page

Item (30), add:  
-- (30) Foreign Application Priority Data  
May 28, 2015 (CN) ............................... 201510282892.3 --

Signed and Sealed this  
Twenty-third Day of February, 2021

Drew Hirshfeld  
*Performing the Functions and Duties of the*  
*Under Secretary of Commerce for Intellectual Property and*  
*Director of the United States Patent and Trademark Office*